(12) United States Patent
Maurin et al.

(10) Patent No.: US 6,488,928 B1
(45) Date of Patent: Dec. 3, 2002

(54) PRODUCT FOR TOPICAL APPLICATION CONTAINING A LIPASE AND A HYDROXY ACID PRECURSOR

(75) Inventors: Emmanuelle Maurin, L'Isle-Adam (FR); Daniel Sera, L'Hay les Roses (FR); Gerard Guth, Montmorency (FR)

(73) Assignee: L'Oreal, Paris (FR)

( * ) Notice: Subject to any disclaimer, the term of this patent is extended or adjusted under 35 U.S.C. 154(b) by 1252 days.

(21) Appl. No.: 08/547,124

(22) Filed: Oct. 24, 1995

(30) Foreign Application Priority Data

Oct. 24, 1994 (FR) .............................. 94 12685

(51) Int. Cl.$^7$ .................. A61K 38/46; A61K 31/60; A61K 31/235; A61K 31/22
(52) U.S. Cl. .................. 424/94.6; 514/159; 514/543; 514/546; 514/547
(58) Field of Search .................. 424/94.6; 514/159, 514/547, 546, 543

(56) References Cited

U.S. PATENT DOCUMENTS

| | | | |
|---|---|---|---|
| 4,540,567 A | * 9/1985 | Oneto et al. ................... | 424/45 |
| 4,556,554 A | * 12/1985 | Calvo .......................... | 424/70 |
| 5,407,677 A | * 4/1995 | Tominaga et al. .......... | 424/401 |
| 5,439,935 A | * 8/1995 | Rawlings et al. ........... | 514/451 |

FOREIGN PATENT DOCUMENTS

| EP | A-0 599 819 | | 1/1994 |
|---|---|---|---|
| FR | A-2 211 209 | | 7/1974 |
| FR | A-2 556 218 | | 6/1985 |
| GB | 1470355 | * | 4/1977 |
| WO | WO-A-83 03061 | | 9/1983 |

OTHER PUBLICATIONS

Lyght, C.E. et al., The Merck Manual (11$^{th}$ Ed.), Merck Sharp & Dohme Research Laboratories, Rahway, N.J. (1966), pp. 1390–1395.*
WPIDS Abstract 93–296522 (1993), EP 561195 A1.*
WPIDS Abstract 76–03891X (1976), BE 830830.*
Shimizu, Patent Abstracts of Japan, vol. 12, No. 333 (C–526) [3180], corresponding to JP–A–63 096109, Apr. 27, 1988.
Mori et al, Patent Abstracts of Japan, vol. 14, No. 294 (C–732) [4237], corresponding to JP–A–02 096510, Apr. 9, 1990.

* cited by examiner

Primary Examiner—Russell Travers
Assistant Examiner—S. Jiang
(74) Attorney, Agent, or Firm—Oblon, Spivak, McClelland, Maier & Neustadt, P.C.

(57) ABSTRACT

The present invention concerns a product for topical application, capable of releasing a hydroxy acid on the skin, containing a lipase as enzyme and at least one precursor of the hydroxy acid. The precursor is an ester of the hydroxy acid, containing at least one ester functional group having a saturated or unsaturated, linear or branched chain and from 2 to 25 carbon atoms. According to a preferred form, the precursor and the lipase are packaged so as not to be in contact with one another until the time of application to the skin.

16 Claims, No Drawings

PRODUCT FOR TOPICAL APPLICATION CONTAINING A LIPASE AND A HYDROXY ACID PRECURSOR

BACKGROUND OF THE INVENTION

1. Field of the Invention

The present invention concerns a product for topical application which is capable of releasing a hydroxy acid on the skin, and the use thereof in imparting softness to the skin, including the scalp. The present invention also concerns a process for the cosmetic and/or dermatological treatment of the skin, particularly for the treatment of acne, wrinkles and fine lines, and the use of the present product therein.

2. Discussion of the Background

Hydroxy acids are increasingly used in the cosmetics or dermatological fields for caring for the face and/or the body, and more especially, for giving the face a luminous and radiant complexion, and therefore a healthy, smooth and younger appearance, and for causing the disappearance of blackheads due to acne.

Unfortunately, hydroxy acid compounds are generally provided in compositions having a pH of less than or equal to 4, for the purpose of maintaining the activity of these acids. The application of these compositions to the skin has the major disadvantage of causing stinging, itching and stabbing pains, which can produce great discomfort. The use of these acidic compositions for users with sensitive skin is therefore often out of the question.

There thus remains the need for a cosmetic and/or dermatological product containing hydroxy acid compounds which confers, in particular on the skin, a healthy appearance and rejuvenation, and which is capable of treating acne, wrinkles and fine lines, while minimizing or eliminating the risk of user discomfort.

SUMMARY OF THE INVENTION

Accordingly, one object of the present invention is to provide a novel composition which provides hydroxy acid compounds in an active form, but which reduces or eliminates the risk of discomfort associated with conventional hydroxy acid-containing compositions.

A further object of the present invention is to provide a novel method for administering hydroxy acid compounds to the skin of persons in need thereof, which reduces or eliminates the risk of discomfort which accompanies conventional hydroxy acid-containing compositions.

A further object of the present invention is to provide a novel composition and method for providing hydroxy acid compounds to persons having sensitive skin.

A further object of the present invention is to provide a novel composition and method for treating acne, which reduces or eliminates the risk of discomfort caused by conventional hydroxy acid-containing compositions.

These and other objects of the present invention, which will be readily understood in the context of the following detailed description of the preferred embodiments, have been provided by a composition for topical application, comprising (a) a lipase, and (b) an ester of a hydroxy acid compound, in which the ester functional group contains a saturated or unsaturated, linear or branched carbon chain having from 2 to 25 carbon atoms, which may be substituted.

DESCRIPTION OF THE PREFERRED EMBODIMENTS

The present Inventors have unexpectedly found that the use of a specific enzyme, lipase, in combination with esters of hydroxy acids, progressively releases hydroxy acid compounds on the skin, and thus, overcomes the aggressive nature of the hydroxy acids and consequently avoids the disadvantages of conventional hydroxy acid-containing cosmetic and/or dermatological compositions.

Consequently, the present invention concerns a product for topical application, comprising a lipase and an ester having a saturated or unsaturated, linear or branched chain of from 2 to 25 carbon atoms.

In the context of the present application, "product" refers to both cosmetic and dermatological compositions, as well as commercial devices comprising a container in which the enzyme and precursor components are housed in isolation from one another.

The present hydroxy acid ester/lipase combination makes it possible to control the release of the hydroxy acid, and therefore reduce the risk of discomfort. The present composition also makes formulation easy as a result of improved compatibility of the esters with the media commonly used in the cosmetic and dermatological fields. In particular, the present product can be used without disadvantage or discomfort by people having sensitive skin, in particular because the composition may be formulated at a pH in the region of 6 (e.g., the present composition or a component in the present product may be formulated at a pH of from 5 to 8, preferably from 5.5 to 7.5, and more preferably, from 5.7 to 7.0).

Lipase is an enzyme which hydrolyses triglycerides to diglycerides, monoglycerides, glycerol and/or free fatty acids. It is used in particular in detergents (see the article "Lipases as detergent components", H. Andree et al., *Journal of Applied Biochemistry*, 1980, vol. 2, pages 218 to 229) to remove greasy stains such as those arising from frying fats, oils, sebum or greasy cosmetics such as lipsticks. Due to its ability to hydrolyze triglycerides, it has been used in the cosmetics field in the immobilized form for cleaning the skin (see, for example, U.S. Pat. No. 4,556,554).

The lipase used in the present invention should be sufficiently stable to retain its enzymatic activity. Preferably, the lipase used in the present invention belongs to the group of enzymes of EC 3.1.1.3. classification, which corresponds to a lipase which hydrolyses the ester bonds at the 1- and 3-positions of a triglyceride. It can be chosen, for example, from those sold under the tradenames "LIPASE SP644" and "LIPOLASE 100 L" by the company Novo Nordisk.

The lipase may be included in the present product in an amount of from 0.05% to 30% by weight, preferably from 0.1 to 10% by weight, and more preferably from 0.1 to 5% by weight with respect to the total weight of the composition (e.g., the combination of lipase, ester, cosmetically and/or dermatologically acceptable medium or carrier, additives, adjuvants, etc., not including the weight of any container or packaging in which the composition is contained).

The hydroxy acids to which the present invention applies may be α-hydroxy acids or β-hydroxy acids; may have a linear, branched or cyclic carbon framework; and may be saturated or unsaturated. Hydrogen atoms in the carbon chain of the hydroxy acid can, in addition, be substituted by halogens or halogenated alkyl, acyl (preferably alkylcarbonyl), acyloxy (preferably alkylcarbonyloxy), alkoxycarbonyl or alkoxy radicals, each of which may have from 2 to 18 carbon atoms. Preferably, the term "acyl" refers to a group of the formula —C(=O)—R, where R is an alkyl group having from 1 to 24 carbon atoms or an alkenyl or alkynyl group having from 2 to 24 carbon atoms which may contain one or more sites of ethylenic unsaturation and which may be substituted.

The hydroxy acids which are the most widely used in cosmetics are, in particular, glycolic, lactic, malic, tartaric, citric, 2-hydroxyalkanoic, mandelic and salicylic acids, and their $C_1$- to $C_{22}$-alkylated derivatives, such as 5-(n-octanoyl) salicylic acid, 5-(n-dodecanoyl)salicylic acid or 2-hydroxy-3-methyl-benzoic acid. Alternatively, $C_1$- to $C_{22}$-alkoxylated derivatives, such as 2-hydroxy-3-methoxybenzoic acid, may be used. Any of these hydroxy acids or derivatives are suitable in the present invention.

The ester used in the present invention is an ester containing one or more ester functional groups having a saturated or unsaturated, linear or branched chain of from 2 to 25 carbon atoms and optionally containing one or more substituents. The ester functional group is preferably one of the formula —O—C(=O)—R (i.e., an ester of the hydroxyl functional group of a hydroxy acid) or a group of the formula —C(=O)—O—R (i.e., an ester of the carboxyl functional group of a hydroxy acid), in which R is as described above.

The carbon chain of the ester functional group is chosen in particular from acyl (preferably as described above), benzoyl, alkylbenzoyl, acylbenzoyl and 2-hydroxyphenylacetyl radicals, which are optionally substituted. The substituent can be, in particular, hydroxyl, hydroxyalkyl of from 1 to 6 carbon atoms, halogen, alkoxy of from 1 to 4 carbon atoms, hydroxyalkoxy of from 1 to 4 carbon atoms or phenyl, and is preferably a hydroxyl radical.

According to a preferred embodiment of the present invention, the carbon chain of the ester functional group has from 12 to 18 carbon atoms.

The present ester may be chosen from esters of fatty alcohols, such as dodecyl, hexadecyl, stearyl, cetyl, myristyl, linoleyl, octyl and oleyl alcohols, esters of butyl, propyl and ethyl alcohols, esters of polyols, such as propylene glycol, butylene glycol, ethylene glycol or glycerol, and mixtures thereof.

According to a more preferred embodiment, the present ester is selected from the group consisting of cetyl salicylate, dodecyl salicylate, cetyl lactate, propyl glycolate, glyceryl lactate, menthyl salicylate and menthyl lactate.

The ester may be included in the present product in an amount of from 0.1 to 20% by weight, and preferably from 1 to 10% by weight, with respect to the total weight of the composition.

According to a first variant of the present invention, the lipase and the precursor are introduced in a single composition which is preferably prepared just before use.

According to a second variant, the lipase and the precursor are packaged so as not to be in contact with one another, for example in two different compositions, each contained in a separate compartment in a product. The separate compositions can either be (a) mixed at the time of application, (b) applied to the skin successively, or (c) successively applied to the skin with a time delay (e.g., one composition can be applied to the skin, then after waiting for a period of time of from, e.g., 30 seconds to 1 hour, the second composition may be applied to the same location).

It is possible, for example, to arrange the compositions in two compartments, which communicate with a shared pipe from which they can exit while simultaneously being mixed, before application of the mixed composition to the skin. Suitable two-compartment packaging devices are, for example, described in the documents FR-A-2,045,559, FR-A-2,105,332, FR-A-2,258,319, FR-A-2,293,375, FR-A-2,586,913, FR-A-2,643,615, U.S. Pat. No. 3,964,643 and U.S. Pat. No. 4,823,985.

It is also possible to produce one of the compositions in an encapsulated form and/or in the form of microcapsules or microgranules immersed in or mixed with the other composition, the microcapsules or microgranules being crushed at the time of application by rubbing against the skin. Thus, the lipase and precursor may be mixed and the free active ingredient released on the skin at the time the composition is applied.

The present product can be used, depending on the active ingredient ester which it contains, for the cosmetic and/or dermatological treatment of the skin.

A further subject of the present invention is the use of the product as defined above for the cosmetic treatment of the skin. In particular, the present invention also concerns a method for combating acne, wrinkles and fine lines non-therapeutically, comprising applying the product as defined above to skin in need thereof.

A further subject of the present invention is a process for cosmetically treating skin, comprising applying to the skin, simultaneously or after a time delay, a lipase and at least one precursor of a hydroxy acid, wherein the precursor is an ester containing at least one ester functional group having a saturated or unsaturated, linear or branched chain of from 2 to 25 carbon atoms.

The present product advantageously contains a medium for topical application conventional in the cosmetic and/or dermatological fields. Consequently, an additional subject of the present invention is the use of the product as defined above for preparing a dermatological salve or ointment for the therapeutic treatment of the skin.

Cosmetically and/or dermatologically acceptable media generally comprise water, a mixture of water and a fatty substance, or a mixture of fatty substances.

Fatty substances suitable for use in the present invention include mineral oils (petrolatum, mineral oil), vegetable oils and their hydrogenated derivatives, animal oils, synthetic oils, silicone oils (dimethicone, cyclomethicone), fluorinated oils, fatty alcohols (cetyl alcohol, stearyl alcohol), fatty acids and waxes.

In particular, the product can be provided in the form of aqueous, alcoholic or aqueous/alcoholic solutions, hydrophilic or lipophilic gels, microemulsions, and water-in-oil, oil-in-water, water-in-oil-in-water and oil-in-water-in-oil emulsions, which may have the appearance of a cream or of a gel. Optionally, the present product may be capable of foaming, may be in the form of an aerosol, or alternatively, in the form of a vesicular dispersion containing ionic and/or nonionic lipids. Pharmaceutical dosage forms may be prepared according to conventional methods in the relevent field(s).

The medium for topical application used in the present invention may contain one or more adjuvants or additives conventional in the cosmetic and/or dermatological fields, such as hydrophilic or lipophilic gelling agents, surfactants, hydrophilic or lipophilic active agents, preservatives, antioxidants, solvents, fragrances, fillers, screening agents and coloring materials.

The amounts of the various constituents of the present product may be those amounts conventionally used in the cosmetic and/or dermatological fields.

The present product can in particular constitute protection, treatment or care compositions for the face, for the neck, for the hands or for the body, or compositions for the hair, and in particular for caring for the scalp, for example in the form of shampoos, treatment lotions, styling creams, styling gels, or lotions or gels for combating hair loss.

Other features of the present invention will become apparent in the course of the following descriptions of exemplary embodiments which are given for illustration of the invention, and are not intended to be limiting thereof. The examples which follow are given by way of illustration in order to make the invention better understood. The amounts indicated are percentages by weight.

EXAMPLES

Example 1

Care Cream
A. Emulsion Containing the Hydroxy Acid Ester
Oily Phase

| | |
|---|---|
| Steareth-2 (surfactant) | 3% |
| Steareth-21 (surfactant) | 2% |
| PPG-15 stearyl ether (surfactant) | 9% |
| Cetyl alcohol | 2% |
| Stearyl alcohol | 1.5% |
| Petrolatum | 5% |
| Dodecyl salicylate | 2% |
| Cyclomethicone | 3% |

Aqueous Phase

| | |
|---|---|
| Propylene glycol (humectant) | 4% |
| PEG-20 | 5% |
| Phenoxyethanol (preservative) | 0.5% |
| Water | q.s. for 100% |

B. Emulsion Containing the Lipase
Oily Phase

| | |
|---|---|
| Steareth-2 (surfactant) | 3% |
| Steareth-21 (surfactant) | 2% |
| PPG-15 stearyl ether (surfactant) | 9% |
| Cetyl alcohol | 2% |
| Stearyl alcohol | 1.5% |
| Petrolatum | 5% |
| Cyclomethicone | 3% |

Aqueous Phase

| | |
|---|---|
| Propylene glycol (humectant) | 4% |
| PEG-20 | 5% |
| Phenoxyethanol (preservative) | 0.5% |
| Lipolase 100 L | 8% |
| Water | q.s. for 100% |

The emulsions A and B are arranged in two separate compartments and mixed at the time of application to the skin.

Example 2

Care Cream
A. Emulsion Containing the Hydroxy Acid Ester
Oily Phase

| | |
|---|---|
| Triceteareth-4 phosphate/sodium $C_{14}$–$C_{17}$ alkyl sec sulphonate (HOSTACERIN CG from Hoechst Celanese) (surfactant) | 10% |
| Cetyl alcohol | 1% |
| Stearyl alcohol | 1.5% |
| Petrolatum | 2% |
| Mineral oil | 4% |
| Dimethicone (SILICONE L45 from Union Carbide) | 3% |
| Dodecyl salicylate | 2% |
| Cyclomethicone | 3% |

Aqueous Phase

| | |
|---|---|
| Propylene glycol (humectant) | 2% |
| PEG-20 | 2% |
| Phenoxyethanol (preservative) | 0.4% |
| Water | q.s. for 100% |

B. Emulsion Containing the Lipase
Oily Phase

| | |
|---|---|
| Triceteareth-4 phosphate/sodium $C_{14}$–$C_{17}$ alkyl sec sulphonate (HOSTACERIN CG from Hoechst Celanese) (surfactant) | 10% |
| Stearyl alcohol | 1% |
| Petrolatum | 2% |
| Mineral oil | 4% |
| Dimethicone (SILICONE L45 from Union Carbide) | 3% |
| Cyclomethicone | 3% |

Aqueous Phase

| | |
|---|---|
| Propylene glycol (humectant) | 2% |
| PEG-20 | 2% |
| Phenoxyethanol (preservative) | 0.4% |
| LIPOLASE SP 644 | 8% |
| Water | q.s. for 100% |

The emulsions A and B are arranged in two separate compartments and mixed at the time of application to the skin.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A cosmetic method for reducing the appearance of wrinkles or fine lines of skin, comprising, applying to skin in need thereof a composition comprising a lipase and at least one precursor of a hydroxy acid, wherein said precursor is an ester containing at least one ester functional group having a saturated or unsaturated, linear or branched carbon chain of from 2 to 25 carbon atoms, which may be substituted.

2. The method according to claim 1, wherein the lipase and at least one precursor of a hydroxy acid are applied simultaneously or after a time delay.

3. The method according to claim 2, wherein the lipase and at least one precursor of a hydroxy acid are applied simultaneously.

4. The method according to claim 1, wherein the carbon chain of the ester functional group is selected from the group consisting of acyl, benzoyl, alkylbenzoyl, acylbenzoyl and 2-hydroxyphenylacetyl radicals, which are optionally substituted.

5. The method according to claim 1, wherein the carbon chain of the ester functional group has from 12 to 18 carbon atoms.

6. The method according to claim 1, wherein the ester is selected from the group consisting of hydroxy acid esters of dodecyl alcohol, hexadecyl alcohol, stearyl alcohol, cetyl alcohol, myristyl alcohol, linoleyl alcohol, octyl alcohol, oleyl alcohol, butyl alcohol, propyl alcohol, ethyl alcohol, one or more polyols, and mixtures thereof.

7. The method according to claim 1, wherein the hydroxy acid is selected from the group consisting of α-hydroxy acids and β-hydroxy acids.

8. The method according to claim 1, wherein the hydroxy acid is selected from the group consisting of glycolic, lactic, malic, tartaric, citric, 2-hydroxyalkanoic, mandelic and salicylic acids, $C_1$ to $C_{22}$ alkylated derivatives thereof and $C_1$ to $C_{22}$ alkoxylated derivatives thereof.

9. The method according to claim 1, wherein the lipase and the precursor are packaged so as not to be in contact with one another.

10. The method according to claim 9, wherein the lipase and the precursor are packaged in separate compartments.

11. The method according to claim 1, wherein the lipase and/or the precursor are in an encapsulated form.

12. The method according to claim 11, wherein the lipase and/or the precursor are in the form of microcapsules or of microgranules.

13. The method according to claim 1, wherein the lipase is of EC 3.1.1.3. classification.

14. The method according to claim 1, wherein the lipase is present in an amount of from 0.05 to 30% by weight with respect to the total weight of the composition comprising said lipase and said precursor.

15. The method according to claim 14, wherein the lipase is present in an amount of from 0.1 to 10% by weight with respect to the total weight of the composition.

16. The method according to claim 1, wherein the precursor is present in an amount of from 0.1 to 20% by weight with respect to the total weight of the composition.

* * * * *